(12) United States Patent
Flitsch et al.

(10) Patent No.: US 11,000,226 B2
(45) Date of Patent: May 11, 2021

(54) METHODS AND APPARATUS FOR ALIGNMENT OF SENSOR COMMUNICATION DEVICES WITH IMPLANTED BONE HEALING SENSORS

(71) Applicant: Depuy Synthes Products, Inc., Raynham, MA (US)

(72) Inventors: Frederick A. Flitsch, New Windsor, NY (US); Filip Leszko, West Chester, PA (US); George A. Mikhail, Downingtown, PA (US); Randall B. Pugh, Jacksonville, FL (US); Adam Toner, Jacksonville, FL (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 15 days.

(21) Appl. No.: 16/185,050

(22) Filed: Nov. 9, 2018

(65) Prior Publication Data
US 2020/0146624 A1 May 14, 2020

(51) Int. Cl.
*A61B 5/00* (2006.01)
*G16H 40/60* (2018.01)
*A61F 2/48* (2006.01)

(52) U.S. Cl.
CPC .......... *A61B 5/4851* (2013.01); *A61B 5/4504* (2013.01); *A61B 5/681* (2013.01); *G16H 40/60* (2018.01); *A61F 2002/488* (2013.01); *A61F 2250/0002* (2013.01)

(58) Field of Classification Search
CPC ..... A61B 5/4851; A61B 5/4504; A61B 5/681; G16H 40/60; A61F 2250/0002; A61F 2002/488; G01R 27/28; G01R 19/00

USPC ................. 340/4.1; 224/222, 232, 242, 904; 324/655
See application file for complete search history.

(56) References Cited

U.S. PATENT DOCUMENTS

| | | | | |
|---|---|---|---|---|
| 4,135,653 A * | 1/1979 | Sieloff | ...................... | A45F 5/00 224/222 |
| 5,213,242 A * | 5/1993 | de Jong | ............ | A61M 37/0069 224/222 |
| 6,330,961 B1 * | 12/2001 | Borja | ....................... | A45C 1/04 224/221 |
| 6,922,592 B2 * | 7/2005 | Thompson | ........... | A61B 5/0031 607/4 |
| 7,324,850 B2 * | 1/2008 | Persen | ............... | A61N 1/37247 607/30 |
| 7,420,468 B2 * | 9/2008 | Fabian | ..................... | A61B 5/06 340/568.1 |
| 7,549,960 B2 * | 6/2009 | Govari | ..................... | A61B 5/06 600/437 |
| 7,575,550 B1 * | 8/2009 | Govari | ..................... | A61B 5/06 600/424 |
| 7,840,253 B2 * | 11/2010 | Tremblay | ............... | A61B 90/36 600/424 |

(Continued)

*Primary Examiner* — Nam V Nguyen
(74) *Attorney, Agent, or Firm* — KramerAmado

(57) ABSTRACT

The present invention discloses methods and apparatus for fostering wireless communication to and from orthopedic implants. Cuff and bandage devices provide a means of supporting a device which coordinates and optimizes communication with orthopedic implants. The devices support methods which can provide feedback to a user to optimize the signal strength and signal to noise aspects of wireless connections to and from orthopedic implants.

20 Claims, 10 Drawing Sheets

(56) References Cited

U.S. PATENT DOCUMENTS

| | | | | |
|---|---|---|---|---|
| 8,315,687 | B2* | 11/2012 | Cross | A61B 5/04085 |
| | | | | 600/392 |
| 8,474,669 | B2* | 7/2013 | Rohrbach | A45F 5/00 |
| | | | | 224/222 |
| 9,339,660 | B2* | 5/2016 | Feldman | A61N 1/3787 |
| 9,435,830 | B2* | 9/2016 | Joshi | G01R 19/0092 |
| 9,439,566 | B2* | 9/2016 | Arne | A61B 5/0022 |
| 9,504,530 | B2* | 11/2016 | Hartmann | A61B 34/20 |
| 9,532,720 | B2* | 1/2017 | Fujii | A61B 5/02007 |
| 9,533,162 | B2* | 1/2017 | Ter-Petrosyan | A61N 1/37211 |
| 9,575,140 | B2* | 2/2017 | Zur | G01R 33/04 |
| 9,615,650 | B2* | 4/2017 | Soriano | A45F 5/00 |
| 9,717,565 | B2* | 8/2017 | Blair | A61B 90/98 |
| 9,962,199 | B2* | 5/2018 | Forsell | A61B 17/7016 |
| 10,278,779 | B1* | 5/2019 | Rudie | A61B 5/05 |
| 10,314,619 | B2* | 6/2019 | Roschak | A61B 17/7216 |
| 2004/0243148 | A1* | 12/2004 | Wasielewski | A61B 17/00 |
| | | | | 606/130 |
| 2009/0216113 | A1* | 8/2009 | Meier | A61B 5/0002 |
| | | | | 600/424 |
| 2010/0327030 | A1* | 12/2010 | Yang | A45F 5/00 |
| | | | | 224/199 |
| 2013/0123881 | A1* | 5/2013 | Aghassian | A61N 1/3787 |
| | | | | 607/61 |
| 2017/0119318 | A1* | 5/2017 | Shay | A61B 5/05 |
| 2019/0009097 | A1* | 1/2019 | Hartley | A61N 1/37247 |
| 2019/0038214 | A1* | 2/2019 | Mikhail | A61B 5/4504 |

* cited by examiner

METHODS AND APPARATUS FOR ALIGNMENT OF SENSOR COMMUNICATION DEVICES WITH IMPLANTED BONE HEALING SENSORS

BACKGROUND OF THE INVENTION

1. Field of the Invention

The present invention describes an implanted sensor device with an external communication capability. The external communication capability may take the form of a wearable cuff or bandage with signal sensing and optimization capability. In some embodiments, the sensing capability may detect the healing of bones within the body.

2. Discussion of the Related Art

There are numerous types of medical implants that are placed within the body of human patients for various functions. An important and well-established example of implants with a physical function relates to the field of orthopedics and the surgical repair of broken bone, damaged joints and replacement joints. Bone and joint replacement implants provide support functions for the bones they are attached to and the physical characteristics of these implants have understandable importance. Advancements in implants have been made to include sensory functions in the implants. These sensors can monitor numerous aspects of the surgical result, including proper healing, growth and other aspects such as biometrics that correlate with infection.

Historically, the monitoring of proper healing may include the use of radiography. Measurement of infection may be achieved with blood tests, for example, white blood cell count. But these techniques may be too crude to provide sensitive monitoring, whereas sensors at or near the implant site may be configured for very sensitive measurements which may result in superior monitoring of the surgical result, or provide quicker information in a timelier manner, improving the health of the patient and the progress of the healing. Early diagnosis of issues may result in various responses such as antibiotic treatment and tailoring of various therapeutic procedures to improve bone growth rates, effectiveness and improve other factors such as pain levels incurred in patients.

A number of approaches are under development to monitor sensing results at the location of the implants for improved effectiveness. In some approaches, a wire or other means of conveying diagnostic information such as optic fibers may be set during surgery to penetrate the patients skin. The improved monitoring of surgical result progression may justify attaching a patient with a transdermal connection. Nevertheless, a wireless approach may offer clear advantages.

Wireless operation of sensors in bone implants naturally invokes numerous complications ranging from the nature of power sources for the sensing devices to the effectiveness of communication between the sensors and externally located receivers of signals. Wireless communication signals may have complicated pathways for efficient radio frequency emissions, and the need to establish connections between wireless sensors imbedded in bone implants and external charging and communications systems which are compact, straightforward and effective is of growing importance in this field.

SUMMARY OF THE INVENTION

Accordingly, methods and apparatus to support the effectiveness of connections between externally located devices and implanted bone sensing devices are described herein. In some examples, external charging and communications devices are formed as cuff devices that are tightly located above a region containing an implanted sensor with a strap that holds the charging and communications devices in place. These cuff devices may include or may be connected to electronic circuits and software which interact with a user via a display device to give feedback about optimal placement in an external location and configuration. In other examples, bandage type form factors are described where a sensor is located in proximity to the skin of a user through an adhesive on a bandage which may be attached to an external charging and/or communications device. In some examples, alignment marks, for example, temporary tattoos may be imparted to the skin of a user which may align with associated marks on the bandage device to position the device in a desirable location and configuration. In still further examples, the external charging and communications devices may include arrays of antennas or signal receivers which may be optimized by electronics internal to the device to receive communication signals from the sensing devices.

One general aspect of the invention includes an apparatus for positioning a sensor communication device, the apparatus comprising a first band of flexible material including a first portion of a fastening device, a second band of flexible material including a second portion of the fastening device, where engagement of the first portion of the fastening device with the second portion of the fastening device holds the apparatus for positioning a sensor communication device in place in close proximity to an orthopedic implant of a patient, a support structure, where a first side of the support structure is affixed to an edge of the first band of flexible material and a second side of the support structure is affixed to an edge of the second band of flexible material, where the first side of the support structure is in a distal configuration to the second side of the support structure, and the sensor communication device is held by the support structure, where the sensor communication device is capable of communicating one or more of data or power to the orthopedic implant of the patient.

Implementations may include one or more of the following features. The apparatus for positioning a sensor communication device where the sensor communication device includes an antenna that communicates one or more of data or power to the orthopedic implant. The apparatus may also include examples where the sensor communication device includes a plurality of antennas that communicate one or more of power or data to the orthopedic implant. The apparatus may also include an electrical circuit that controls communication and adjusts a directional position and a power level of each of the plurality of antennas. The apparatus may also include an antenna for communicating in a wireless protocol with a data processing device, server, smart device, or mobile communication device. The apparatus may also include a support structure which allows the sensor communication device to be rotated around an axis. The apparatus may also include a display screen, where the display screen provides feedback to a user to adjust a rotational position of the sensor communication device, where the adjustment optimizes signal communication between the sensor communication device and the orthopedic implant. The apparatus may also include examples where the first band of flexible material includes medical grade fabric, medical grade plastic, or Velcro® brand products. The apparatus may be located within a limb, on the spine, or within the head. The sensor communication device may be held upon the support structure by an adhesive or by Velcro® brand products. The apparatus may also hold the sensor communication device upon the support.

One general aspect of the invention may include an apparatus for positioning a sensor communication device which may include an adhesive layer, wherein the adhesive attaches to a user's skin and may be released with an amount of force safe for the user's skin. The aspect may also include examples wherein the adhesive holds the apparatus for positioning a sensor communication device in place on the user's skin in close proximity to an orthopedic implant of a patient. The apparatus may also include a support structure, wherein a first side of the support structure is in contact with the adhesive layer and a second side of the support structure provides a support layer for the sensor communication device. There may be examples wherein the sensor communication device is capable of communicating one or more of data or power to the orthopedic implant of the patient.

One general aspect of the invention includes a method of receiving data from an orthopedic implant, the method including placing an apparatus for positioning a sensor communication device in proximity to an orthopedic implant which has been implanted into a patient, holding a sensor communication device with the apparatus for positioning a sensor communication device, providing a signal from the sensor communication device to the orthopedic implant, where the signal initiates the orthopedic implant to send out a communication, receiving a signal from the orthopedic implant to the sensor communication device, rotating the sensor communication device around an axis, where the signal from the orthopedic implant is continuously sensed by the sensor communication device, analyzing the sensed communication signals to determine an orientation of maximal signal to noise, displaying a message to a user to rotate the sensor communication device, rotating the sensor communication device, displaying a message to the user when the rotation is at the maximal position to suspend moving the device, and receiving a communication from the orthopedic implant of a result from a sensor on the orthopedic implant. Other embodiments of this aspect of the invention include corresponding computer systems, apparatus, and computer programs recorded on one or more computer storage devices, each configured to perform the actions of the methods.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Figure 1A:
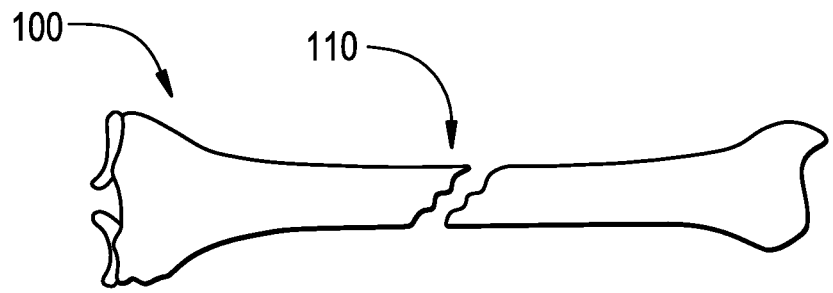
FIGS. 1A and 1B illustrate exemplary bone implant arrangements for a damaged bone wherein the bone implant may contain sensors of various types in accordance with the present invention.

The present invention includes methods and apparatus for interacting and transferring data from monitoring sensors that may be implanted in a patient onto a healing bone. Sensors may be incorporated into standard orthopedic implants or into standard hardware of orthopedic implants such as screws and plates, or the sensors may be an individual component implanted into the patient. A sensor reading device may receive monitoring data from the implanted sensor. In addition, the present invention includes methods and apparatus for aligning the sensor reading device with respect to the sensor, for optimal data transfer. Discussions about feedback devices, which may include applications running on smart phone devices or other handheld devices, may be utilized to display the status of alignment and are also included herein.

According to the present invention, a sensor may be placed in proximity to a healing bone in such a way that it may mechanically track the progress of the healing process and feed the data from this monitoring into a communication device so that a doctor or other user may use this data for some means. In some embodiments, the implanted sensor may be passive, where the sensor reading device measures the sensor's current state with respect to other data readings taken previously. The sensor reading device may comprise an energy source and a means for mounting onto the body of the person with the healing bone such that data may be gathered during active use of the healing bone.

Bone healing involves a complex and sequential process to restore the bone to its pre-fractured condition. For normal healing to occur, the fragments of the bone must be viable, the bone must be at mechanical rest, for example, through immobilization via cast and/or internal fixation, and there must be no infection. The healing process differs depending on the nature of the fracture. The healing process may be broadly classified as spontaneous healing, contact healing and gap healing.

In spontaneous healing the fracture ends are positioned close to one another and secured in position. A hematoma forms proximate the fracture and initiates the healing process. Within the first forty-eight (48) hours, chemotactic signaling mechanisms attract inflammatory cells required to promote the healing process. Within seven (7) to fourteen (14) days, granulation tissue is formed between the bone sections which leads to the vascularization of the hematoma. Progenitor cells in the granulation tissue proliferate and differentiate into chondroblasts and fibroblasts and produce an extracellular matrix of cartilage and fibrous tissues and woven bone is deposited by osteoblasts. This portion of the healing process may take from four (4) to sixteen (16) weeks. During this time the woven bone is replaced by lamellar bone. Finally, in the last step of the healing process, the bone is remodeled thereby restoring its cortical structure. Remodeling may continue for years.

In contact healing, apposed bone fragments that are spaced apart less than 0.1 mm are typically rigidly fixed relative one another to reduce interfragmentary strain. The contact healing process is initiated by osteoclasts forming cutting cones that traverse the fracture. Capillaries then form in the cavities that are formed along with endothelial cells and osteoblasts progenitor cells that form lamellar bone from osteons. If internal fixation leaves a gap of less than 1 mm between bone fragments, lamellar bone formation as described above is preceded by the formation of woven bone scaffolding. This process is known as gap healing.

In all bone healing processes, there are numerous risk factors that may influence the healing process, including insufficient immobilization or fixation, soft tissue interposition, bone loss, drug and/or medication interference, metabolic disease, poor nutrition and infection, which is discussed in greater detail below. The sensors of the present invention may be able to detect the presence and/or absence of certain materials in addition to measuring stress, strain and/or elongation that may indicate whether a fracture is healing properly.

Bone Healing Sensor

Figure 1B:
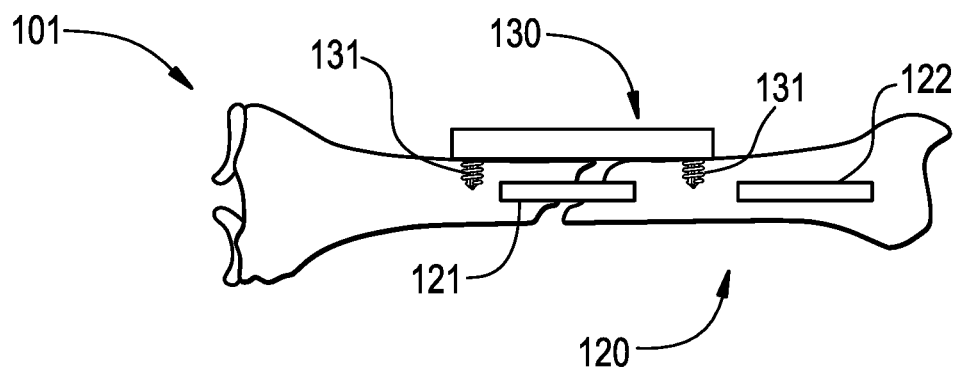

Referring to FIG. 1A, a damaged bone 100 is illustrated. After repairing the damaged bone 100 the healing process may be monitored for any number of relevant parameters as described in greater detail herein. Referring to FIG. 1B, a monitored healing bone 101, with a sensing system 120 successfully implanted, is illustrated. As in FIG. 1A the damaged bone 100, may have some form of damage 110, for example, a fracture, or other type of injury, where the healing progress following an operation to mend the damage 110 may be desired to be monitored. This damage 110 may include, as a non-limiting example, a complete breaking of the bone, where the natural healing process of the break may induce a mechanical change in the structure of the bone that may be measured by an electromechanical device, such as a stress sensor.

During a medical procedure or surgery to mend the injury, a monitored healing bone 101 may be secured with plates 130, or other mechanical instrumentation that secures the healing parts of the monitored healing bone 101 together. During the surgery to secure the monitored healing bone 101 with the plate 130 held in place by fastening elements 131, a sensing system 120 may also be secured to the monitored healing bone 101, that may be used to collect relevant data on the healing process. The fastening elements 131 may include any suitable structures, for example, screws or pins. In a non-limiting example, this sensing system 120 may consist of two separate stress sensors. An active sensor 121 may be placed to span the damage 110, where each end of the active sensor 121 is affixed to each respective side of the healing bone 101. In alternate exemplary embodiments, the sensor 121 may be positioned on the fixation device itself.

Since fractures can range in size and surgeon typically do not utilized two plates as that may make it too stiff for healing, the sensors may be positioned on the plate itself. In this way, as a stress sensor, the measured level of stress may be indicative of the relative displacement of the two sides of the healing bone 101. The resulting stress/displacement data curve, over the course of the healing process, may be compared against an expected stress/displacement curve for the type of injury.

In its functional states, many of these kinds of sensors may be exposed to an implicit level of electrical noise that is imparted to their determination of sensing results or in the process of the transference of data. These levels of electrical noise may be caused by the inherent functioning of the device, interference with outside sources of electromagnetic radiation, or other means. To account for this noise, a second sensor 122 may be placed in proximity to the active sensor 121. However, this second sensor 122 may be placed in a position that does not span the damage 110. In this way, the second sensor 122 may be exposed to any outside source of noise that also affects the active sensor 121. A result from sensing the active sensor 121 may be simultaneously read by a sensor communication device that reads the second sensor 122. In such an example, the active sensor 121 may convey the relevant data plus noise, and the second sensor 122 may convey the same noise, so that the second sensor 122 data may be subtracted from that of the active sensor 121, to yield an improvement in signal to noise metrics of the relevant data.

Figure 1C:
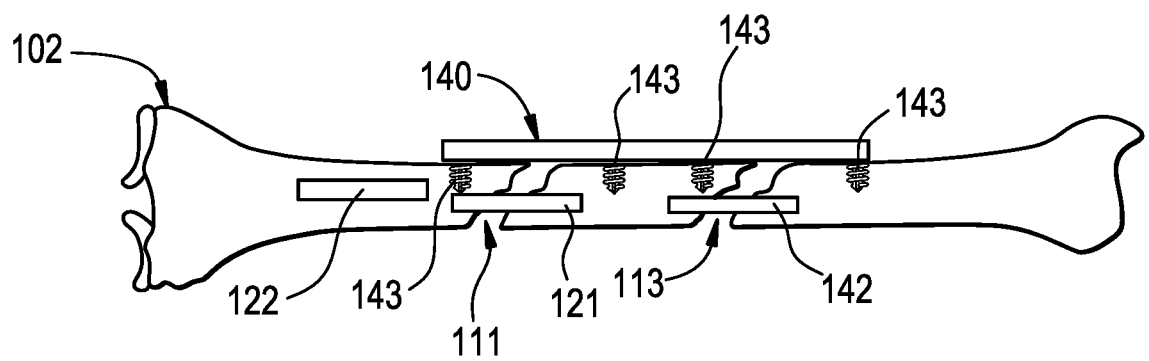
FIG. 1C illustrates a complex damaged bone with exemplary bone implant arrangements, wherein the bone implants may contain sensors of various types in accordance with the present invention.

Referring now to FIG. 1C, a monitored healing bone 102 with multiple instances of damage 111 and 113 may be seen. The damaged areas 111 and 113 may be secured with a single plate. Multiple plates are typically not utilized as it may make healing more difficult. The plate 140 is secured in place with fasteners 143. Multiple active sensors 121 and 142 as well as second sensor 122 may be affixed to the monitored healing bone 102, in the case that multiple points need to be monitored for healing. It is important to note that this arrangement represents one exemplary embodiment. In a more preferred embodiment, the sensors may be affixed to the plates. These sensors may act independently from each other and may be accessed separately by sensor communication devices. In addition, as set forth above, it may be desirable or preferred that the sensors or sensors be positioned on the fixation device or plate. The depiction in FIG. 1C is a non-limiting example of a monitored healing bone 102 with multiple instances of damage 111 and 113. Many more complex arrangements of damage may be handled differently, depending on the necessary operation for repairing them, and the sensor arrangement may be adjusted and applied accordingly. The sensors may monitor many different aspects of the bone healing environment including stress, temperature, pH, and oxygen content as non-limiting examples.

Figure 1D:
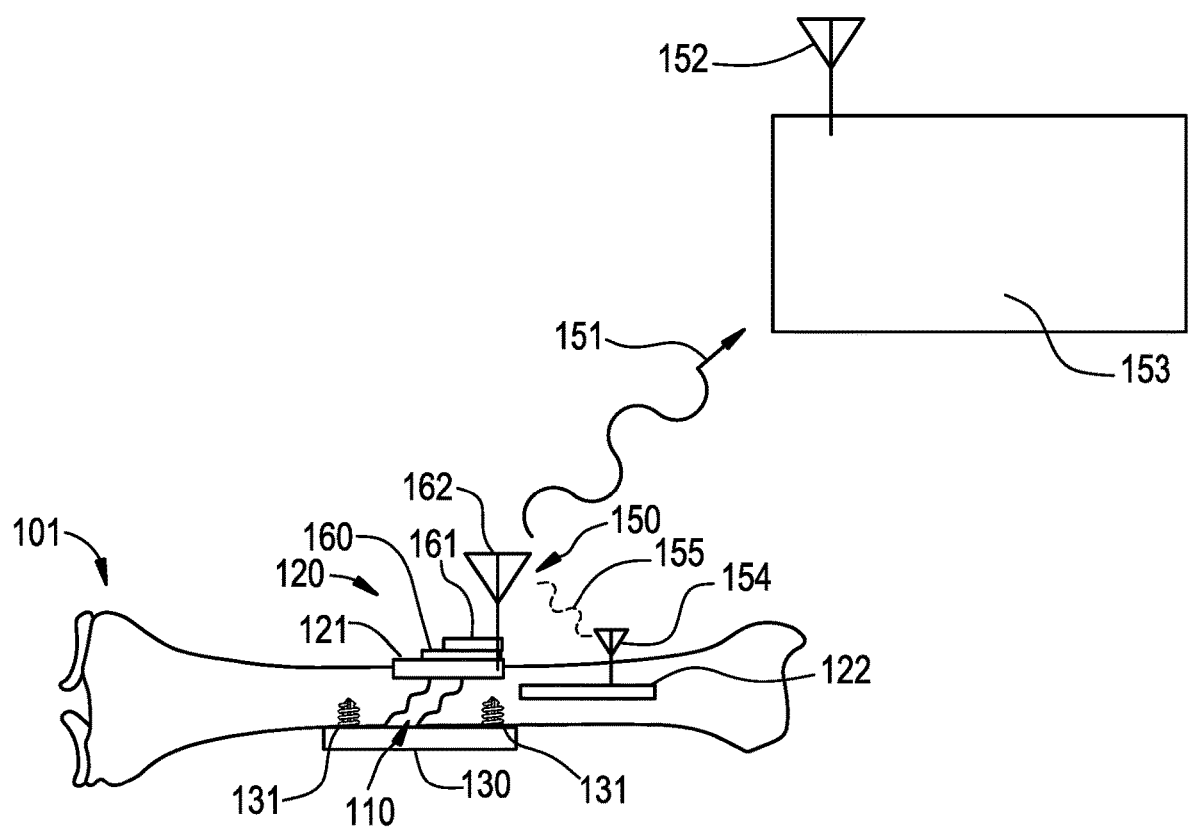
FIG. 1D illustrates an exemplary diagrammatic representation of a bone implant containing a sensor which is in electrical communication with an external communication and power supplying device in accordance with the present invention.

Referring to FIG. 1D, a monitored healing bone 101 may include a wireless transmission function as part of the orthopedic implant. The bone may have damage 110 that is held in place by a plate 130 with fastening elements 131. A sensing system 120 may include an active sensor 121 and a second sensor 122. The active sensor 121 may include a wireless communication system 150 which may transmit a signal 151 through the patient and to a receiving system 152 of an external receiving unit 153. The wireless communication system 160 may comprise an energy storage means which may be charged in a wireless fashion by the wireless communication system 150 or by another wireless charging system. The wireless communication system 150 may also include an antenna or array of antennas configured to communicate data with low power usage that will effectively penetrate tissues of the patient to pass communication onto the receiving unit 153. The sensing system 120 may include sensing elements that measure stress in numerous manners. In some examples, piezoelectric transducers may convert measurements of stress and strain to electrical signals. In some examples, a microscale array of piezoelectric transducers may register sensing results across a measured surface. In other examples, piezoresistive, capacitive and inductive pressure and strain sensors may be used to monitor healing. The desired parameters to be measured or monitored determine the sensors to be utilized.

It is important to note that active sensors, passive sensors and or a combination thereof may be utilized in accordance with the present invention. Active sensors may comprise their own power source such as a battery or fuel cell which may be rechargeable. Passive sensors may only be powered through an external source via an antenna. In addition, as set forth above, it may be desirable or preferred that the sensors or sensors be positioned on the fixation device or plate rather than on the bone.

In some examples, the orthopedic implant may include a housing having an aperture defined therein and a secondary coil positioned in the aperture. The secondary coil may include a number of turns positioned so as to define a reference plane. The reference plane may be substantially parallel to a sagittal plane of a body of a patient in which the orthopedic implant is implanted. The orthopedic implant may also include a processing circuit electrically coupled to the secondary coil. As mentioned previously, the electrical circuitry connected to the secondary coil may be configured to receive a power signal from the secondary coil when the secondary coil is inductively coupled with a primary coil of a charging system. In some examples, control circuitry 160 may require an identification communication before the secondary coil is configured to charge an energy storage device in the implant or in a sensor associated with the implant.

The orthopedic implant may also include a wireless transmitter 161 coupled to the processing circuit and an antenna coil 162 electrically coupled to the wireless transmitter 161. The processing circuit may be configured to control the wireless transmitter 161 to transmit implant identification data in response to the power signal using the antenna coil 162. In some examples, data communication between sensor elements in the sensing system 120 may be performed in a wireless manner between the antenna coil 162 of the main sensor and an antenna coil 154 of the second sensor as illustrated by signal 155.

The orthopedic implant may also include one or more sensors such as, a pressure sensor, a load sensor, a temperature sensor, a pH sensor, an oximetry sensor and/or a hall-effect sensor as non-limiting examples. The processing circuit may be configured to receive an output signal from the sensor(s) and control the wireless transmitter to transmit the output signal in response to the power signal using the antenna coil. The transmitter may be configured to transmit the implant identification data and/or the output data using a wireless frequency. The wireless transmitter may conform to one or more wireless standards and frequencies such as Wi-Fi, Bluetooth, Zigbee, RFID or other wireless standards. For example, the transmitter may transmit the implant identification data and/or the output data at an appropriate frequency. The appropriate signal would depend on the location and surrounding tissue through which the signal must pass.

The orthopedic implant may have functionality for transmitting data while receiving a power signal generated by a remote external primary coil with a secondary coil of the orthopedic implant. The resulting signal may power a battery charging component that is connected to a battery which supplies power to the orthopedic implant. In alternative examples, the power signal may directly power the processing circuit when there is enough received power at the secondary coil. The power signal may directly power the transmitter, a sensing function, control circuitry, memory circuits and other exemplary functions. As set forth above, active sensors, passive sensors and or a combination thereof may be utilized in accordance with the present invention.

It is important to note that various configurations may be utilized to save energy and provide safe and secure communication. For example, to save power, the receiving device may periodically send out a signal to determine if the implanted device is transmitting data. In that instance, if a signal is detected, a "wake-up" signal may be transmitted and then data may be transmitted. With respect to security, unique identifiers may be utilized.

Sensor Communication Device

The human body may provide a challenging environment for an orthopedic implant being able to transmit signals wirelessly from electronic circuits related to the sensors of the implant out of the body and to the receiving devices. Body tissues are dominated by aqueous solutions of relatively high ionic content. As well, bones and the metal of the implant devices may also create challenging environments for wireless transmission. Therefore, selected pathways through a body from an implant to an outside receiver may have optimal transceiving capabilities. The signal to noise at the receiver may have a very sensitive dependence on achieving a proper implant to receiver orientation to align with the appropriate select pathway.

Figure 2A:
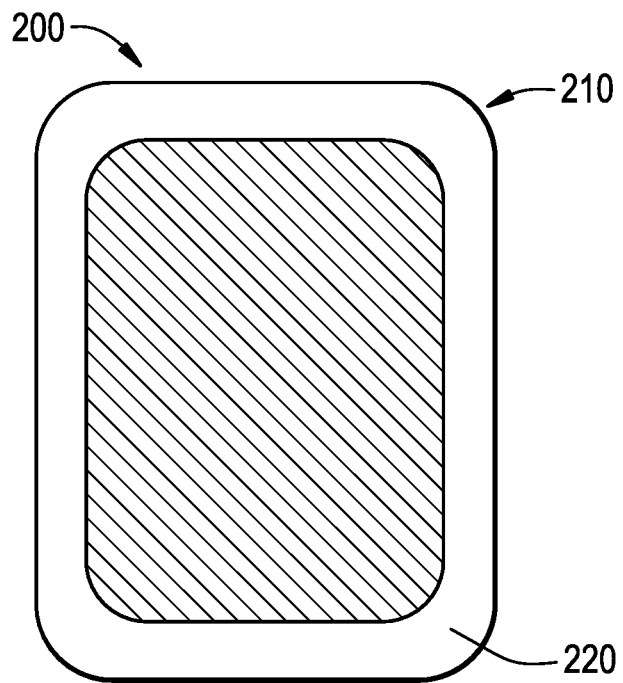
FIG. 2A illustrates an example of a bandage-type device to affix a sensor communication device to a body in proximity to a sensor that it will communicate with in accordance with the present invention.
Figure 2B:
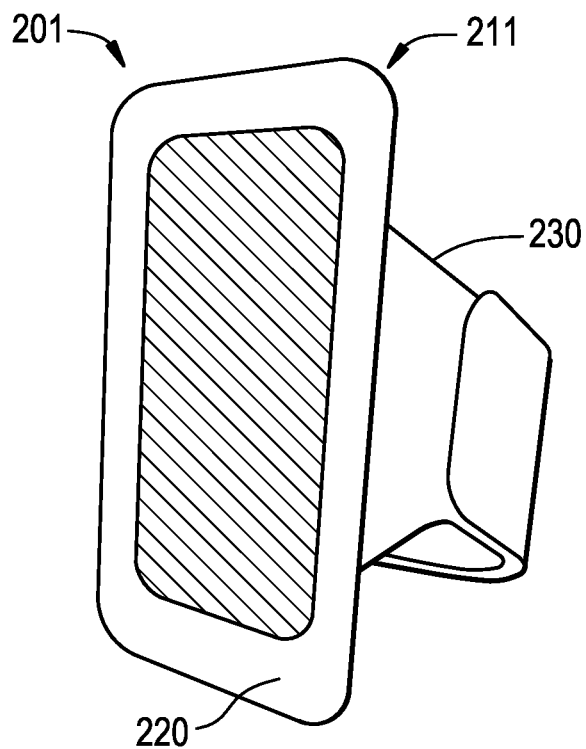
FIG. 2B illustrates an example of a cuff-type device to affix a sensor communication device to a body in proximity to a sensor that it will communicate with in accordance with the present invention.

Referring to FIGS. 2A and 2B, illustrations of exemplary embodiments of devices to affix a sensor communication device in proximity to an imbedded sensor are depicted. Sensors imbedded inside the body, may not be desirably accessed by standard physical means, such as connecting wires. Such wires may create the need for extra surgeries, may result in discomfort for a patient, or may result in unhealthy conditions such as irritation or infection around the interface of the skin with the connecting cables. Therefore, wireless transmission into and out of imbedded implants may provide a more than satisfactory solution. Thus, a wireless data transfer means, to transfer the data collected by the imbedded sensor outside of the body for use, may be desired. A sensor communication device may fulfill the purpose of reading data from a bone healing sensor imbedded inside a patient's body via a wireless means.

In general, the closer that the receiver is placed to the transmitter, the stronger the signal may be and the better the signal to noise ratio may be. In addition, there may be particular alignments that are preferred over others. An apparatus that brings a sensing device into close proximity to the skin near regions proximate to the orthopedic implant can help improve functionality of wireless transfer of data. This is especially helpful when the apparatus that brings the sensing device in close proximity to the skin also allows either movement of the device to maximize signal reception or alignment of the device to an already determined maximal signal capability.

Referring to FIG. 2A, an exemplary device to affix a sensor communication device 200 is illustrated. This device comprises an adhesive skin patch 210, which may be called a "bandage," that holds the sensor communication device 220 in place. The adhesive skin patch 210 may have one face that is coated in a hypoallergenic adhesive, or body adhesive. These types of adhesives are known in the art and are available for long term water-resistant use. The other face of the device to affix a sensor communication device 200 may contain or adhere to an attached sensor communication device 220. As two non-limiting examples, in some embodiments, the attached sensor communication device 220 may be rigidly attached to the adhesive skin patch 210, where the entire package is disposable after one use. In some examples, the adhesive skin patch 210 may have attached hardware for temporarily affixing the sensor communication device 220. In some examples, the adhesive skin patch 210 may have a pocket that allows the sensor communication device 220 to be placed in the pocket and to be rigidly held in an orientation set by the adhesive skin patch 210.

Referring to FIG. 2B, a second exemplary device to affix a sensor communication device 201 is illustrated. This device type may be called a "cuff" form 211 of a device holder. A "cuff" form 211 may be desirable in situations where an adhesive solution is not entirely functional.

As such, this second exemplary device to affix a sensor communication device 201 may include a strap 230 to secure the device to the body. The strap 230 may be made of two parts or two bands which have a means to fasten to each other. The fastening means may include a Velcro® brand product, snaps, buttons, laces and the like. Such a strap 230 as illustrated in FIG. 2B may function to affix the sensor communication device 220 over a limb. Other affixing formats, such as a belt or shoulder strap, as non-limiting examples, may also be used to affix the sensor communication device 220 over other parts of the body. In some non-limiting examples, depending on the desired location for affixing the sensor communication device 220, a body adhesive, as depicted in FIG. 2A, may not provide a secure enough mount for the device, for reasons of moving skin, as a non-limiting example. As such, a strap 230 may provide additional mounting strength to better support the device.

In some non-limiting examples, a patient may desire, or be prescribed, to have extended monitoring of a healing bone. In these cases, it may be desired to affix a sensor communication device to a healing spot multiple times over the course of the healing process. In some examples like this, the exact nature of the alignment of the sensor communication device relative to the skin of the user may change over time. Thus, either a bandage form or a cuff form may include a rotatable base structure onto which the sensor device may be mounted and then subsequently rotated to adjust the orientation of the device relative to the bone implant.

Referring to FIGS. 3A-3D an example is illustrated of how the bandage and cuff devices may support a sensor communication device and allow for movement of the device. In some examples, the sensor communication device may have a display screen that may provide feedback to a user relative to the optimal rotational alignment of the device. The sensor communication device may communicate a signal to the bone implant that is a general signal for the implant device to begin transmitting. This may be a charging signal, an analog signal or a digital signal. Once the bone implant is transmitting, the user may rotate the sensor communication device through a full range of motion. While the device is being rotated it may be continually monitoring the strength of a signal that it receives from the orthopedic implant. An algorithm configured to operate on the sensor communication device may analyze the collected data and then determine an optimal orientation across all the orientations.

Figure 3A:
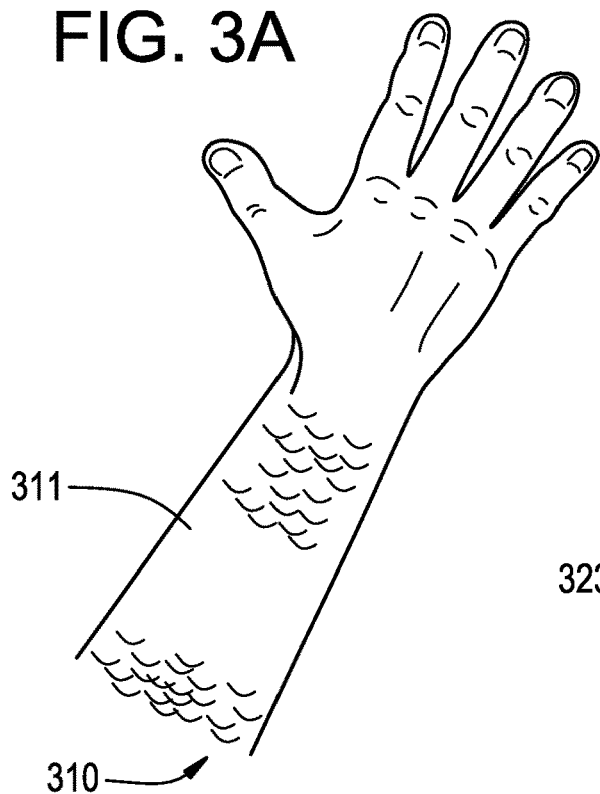
FIGS. 3A-3D illustrates the steps of an exemplary method to align a sensor communication device with a sensor that it will communicate with in accordance with the present invention.
Figure 3B:
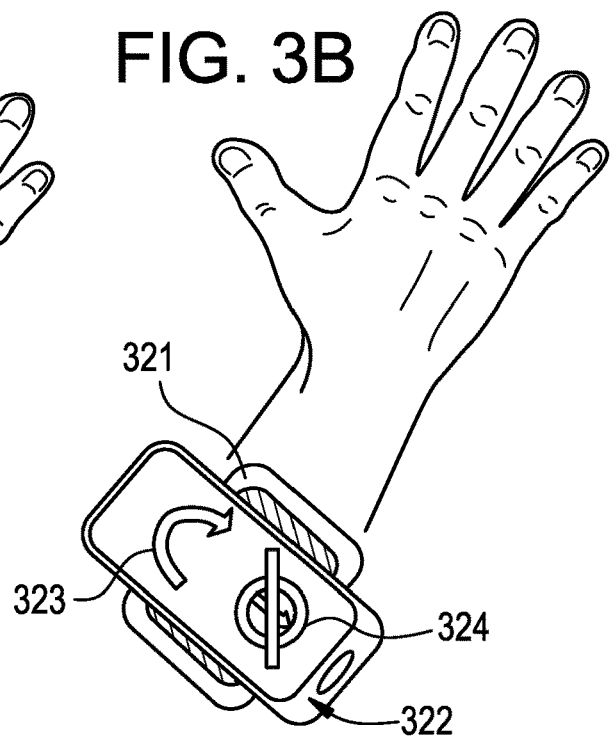
Figure 3C:
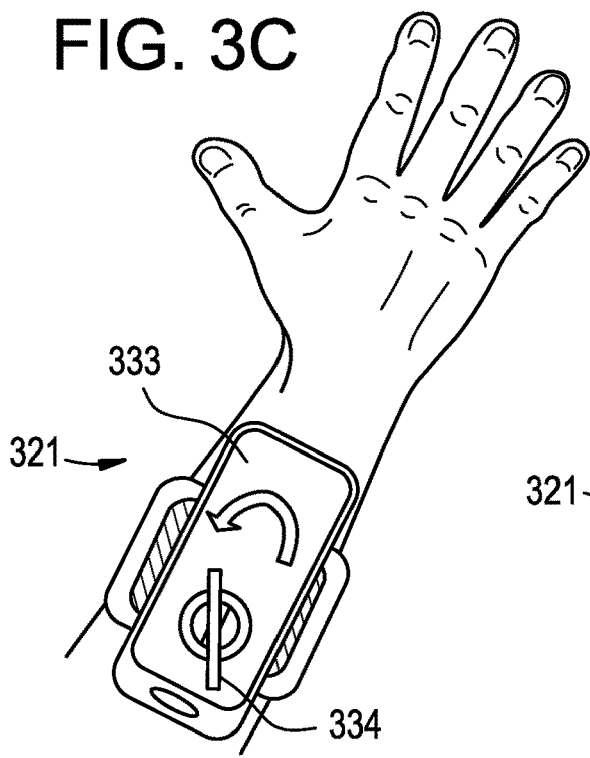
Figure 3D:
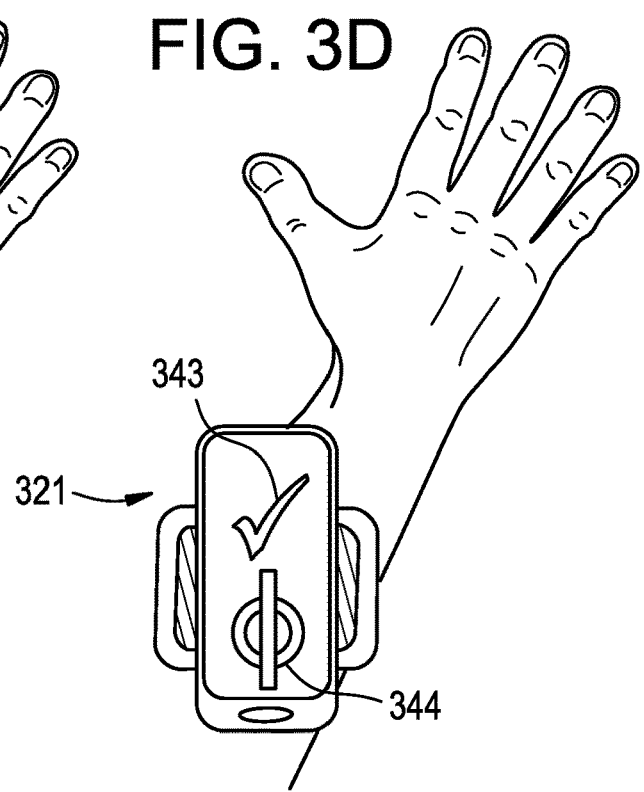

Referring to FIG. 3A, a user's forearm 310 may include an orthopedic implant. For illustration, the user's forearm may be shaven 311 in the vicinity of the desired measurement. It is important to note that shaving is not required. Referring to FIG. 3B, a cuff device 321 may be placed onto the user's forearm with a display screen 322 of the sensor communication device displaying feedback data. As an example, an icon 323 may indicate to the user that they should turn the device to the right or clock-wise. Another icon 324, may pictorially show the alignment of the device relative to the optimal orientation. Referring to FIG. 3C, the user may have rotated the sensor communication device toward the right, perhaps a bit too far. Now, an icon 333 may highlight to the user that they should rotate the device to the left a bit or counter clock-wise a bit. Similarly, another icon 334 may show that the orientation is nearly aligned but not quite so that the movement should be rather small. Proceeding to FIG. 3D, the user may have moved the cuff device 321 in such a way that the sensor communication device is now optimally placed. In this case, an icon 343 may indicate that the alignment is optimal and a second icon 344 may show that the device is aligned on top of the optimal alignment. This alignment procedure may work similarly to an electronic level with both an icon and an auditory signal.

Figure 4A:
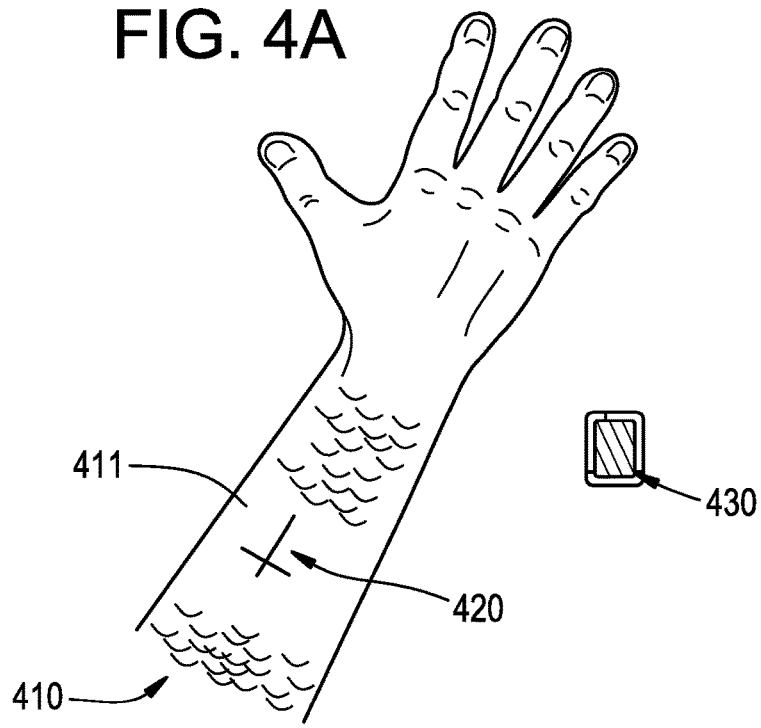
FIGS. 4A-4C illustrate the exemplary steps to affix and align a bandage-type sensor communication device with a sensor that it will communicate with in accordance with the present invention.

As described in relationship to FIGS. 3A-3D, the exemplary methods may be useful for optimizing the rotational alignment of a sensor communication device. The orientation of the device along the forearm, or more generally along a surface of the skin may be precisely measured in an office setting. In some examples, when the optimal location is determined a marking may be made upon the patient's skin that may be used at a later time to align the cuff or bandage device to be in an optimized location, even if a rotational change may be made after that. Referring to FIG. 4A, a user's forearm 410 may have an orthopedic implant inside it. On the surface 411 of the forearm may be a location that is optimally located relative to the orthopedic implant. Measurements may be made to quantify the best location and a marking 420 may be made on the forearm to allow registration of a sensor communication device at future use events. In some examples, the marking 420 may be a temporary, but long-lasting tattoo or skin marker. In an alternative embodiment, the tattoo may be similar to the tattoos utilized in radiation treatment for cancer. While permanent, they are typically very small. In some examples the tattoo may be written with an ultraviolet sensitive ink so that the tattoo may be invisible under normal lighting conditions. The marking 420 may be used to align a bandage device 430 onto the skin. After alignment the bandage device may be fastened to the skin and be able to align the sensor communication device to communicate with the orthopedic implant.

Figure 4B:
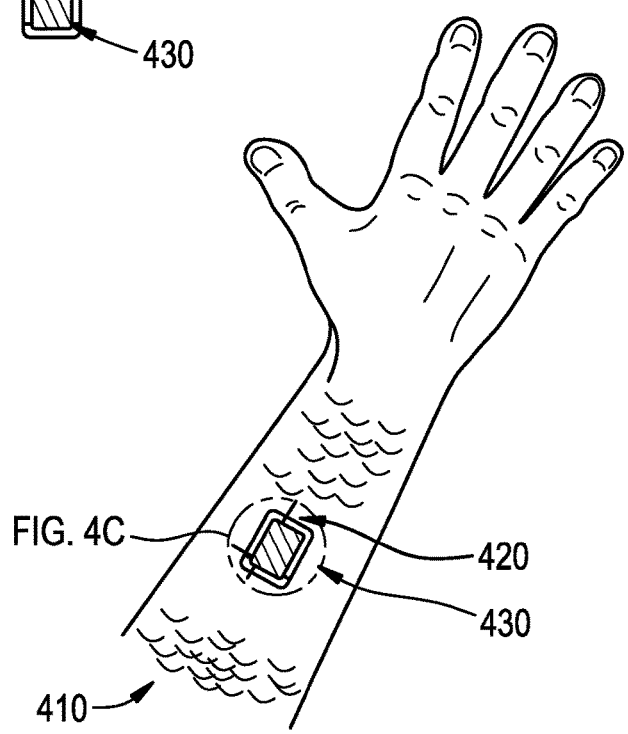
Figure 4C:
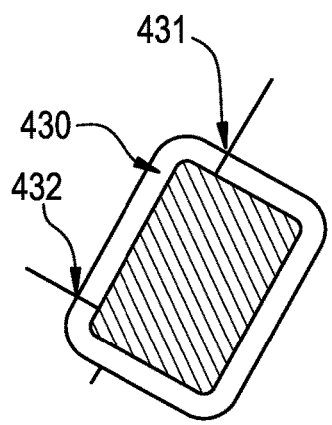

Referring to FIG. 4B, the bandage device 430 may be affixed to the surface of the user's forearm 410 at marking 420. As illustrated in FIG. 4C, the alignment marks of the marking 420 may be aligned with matching marks on the bandage. A first mark 431 on the bandage device may align with a leg of the tattoo and a second mark 432 on the bandage may align with a second leg of the tattoo locating the bandage in a relatively precise location.

Signal Strength Optimization

Figure 4D:
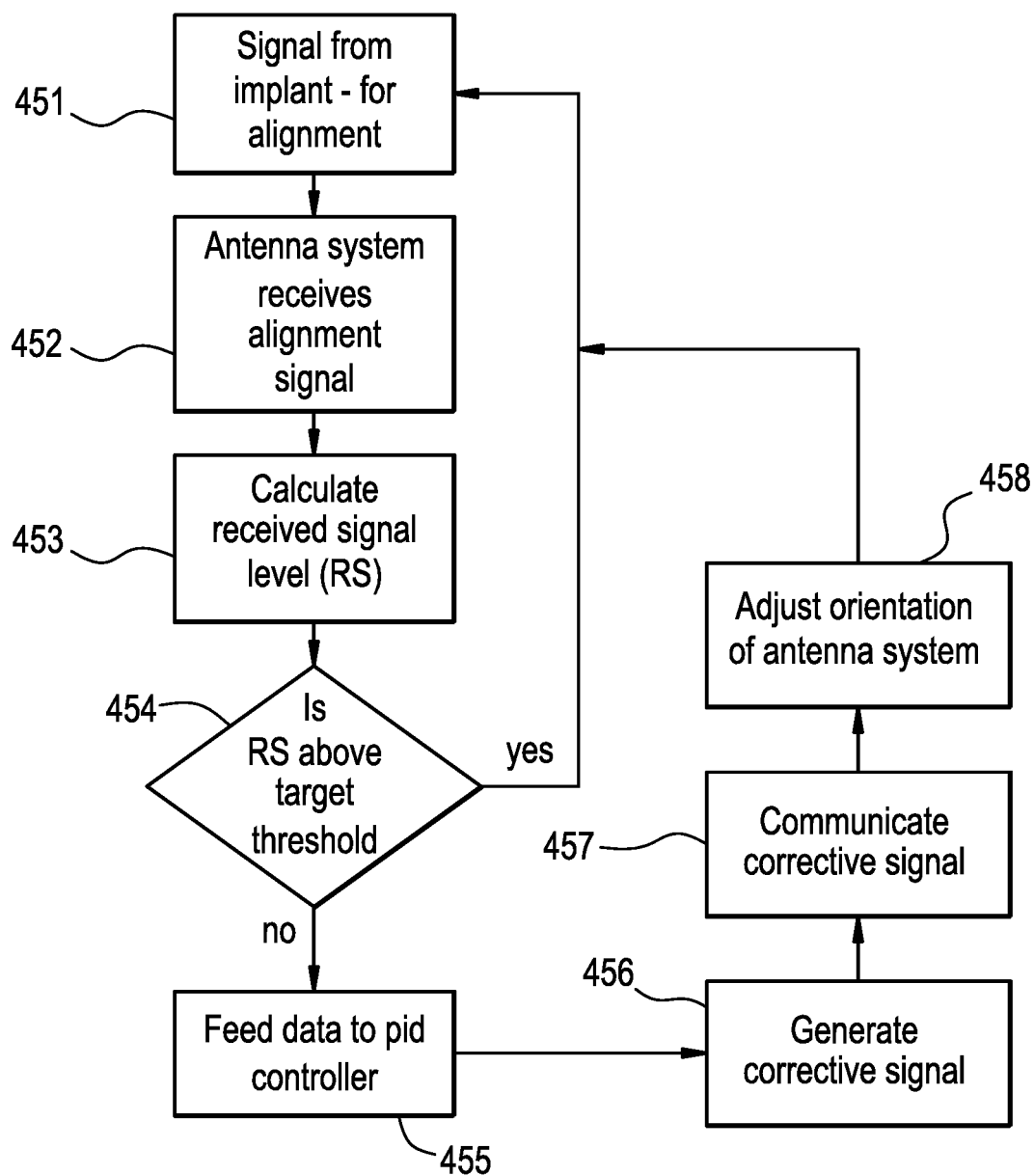
FIG. 4D is a flow chart illustrating an exemplary method to align a sensor communication device in accordance with the present invention.

Referring now to FIG. 4D an exemplary depiction is provided of the flow of processing that may occur when aligning antenna systems of an implant with an external device such as a cuff. In some examples, a transmitting system within the implant may provide a signal stream that is dedicated to the purpose of aligning the transmitter/ receiver of the implant with the external cuff device. The alignment focused signal stream may be transmitted at a slightly different baseband frequency from other data and power transmission-based transmissions. In other examples, the alignment signal may be inserted into and become part of the data stream transmission. The alignment signal may generally comprise a maximal output power component multiplexed into a recognizable sequence with components of reduced output power. In some examples, alignment signals may be broadcast at differing baseband frequencies to allow for potentially improved transmission characteristics in a particular body environment for a particular frequency domain. One or more of these various alignment signal options may be employed by the implanted device at step 451 to transmit the alignment signal to the surrounding environment.

At step 452, an antenna or multiple antennas of an antenna system may receive signals from the implant device. Based on the type of signal being transmitted, the receiver of the alignment system of the cuff may extract the alignment signal and calculate a parametric value, which may be classified as the received signal level (RS as used hereafter) at step 453. In some examples, a mathematical transformation may be employed to generate the received signal level such as expressing the parameter as a logarithm of the parameter or as some other mathematical transform that may represent the nature of the signal strength of absorption that naturally occurs as the external receiving device may be rotated around a point of rotation.

At step 454, a comparison is made between the RS parameter and a target value. In some examples, this comparison may be a digital signal processing step. In other examples, an analog signal may be electronically compared at the step. The result of the comparison may be a digital result of "yes" where the received signal is above a target value and adjustment of the orientation of the cuff or other receiving device may be halted. In such a case, processing may revert to waiting for an alignment signal to be sent by the implant device.

The digital result may be "no" where the signal is still not optimally received. In some examples, the practical aspect of the target threshold may be a relative amount, where a probing of the maximal signal strength possible may have been performed historically and such possible maximal value used with some buffering to determine the desired threshold to pursue further adjustment of the receiving device. In other examples, the threshold value may be related to a minimum value above which acceptable signal-to-noise results of the transmission system may be realized.

Proceeding to step 455, when the RS is beneath the target value, the value of the RS may be fed to a proportional-integral-derivative (PID) control system. In some examples, the PID control system may operate as an algorithmic processor that digitally process a stream of digital data presented to it in the feedback loops of FIG. 4D. In other examples, an analog signal may be fed to an electronic PID controller in step 455. The PID controller will generate a corrective signal, step 456, based on the summation of contributions of proportional responses to the input signal, with responses to the integrated recent time history of the data stream as well as the immediate time rate of change of the signal stream. In some examples, the corrective signal may be communicated to a device which will respond directly to the value once it is communicated to it. In other examples, a communication may be made to a user to adjust the device as has been described previously, and the nature of the value may alter the iconic representation of how much rotation the user should perform such as a thicker arrow, a number count of arrows or the like.

In such examples, the corrective signal may be communicated to the feedback active element at step 457. Next, at step 458 an adjustment to the orientation of the antenna system of the cuff or other receiving device is made. The reception of the alignment signal will then reoccur as shown by the processing reverting to step 451. As may be apparent, the feedback loops may be performed constantly to ensure that the alignment has been appropriately maintained. In some examples, the alignment feedback loops may be utilized as a setup protocol where an exit (not shown) of the processing may occur under certain circumstances such as the attainment of an acceptable signal or a timed duration during which the signal has remained above a threshold level. In some such cases, the antenna system may have protocols that allow for subsequent activation of the alignment processing as described.

Multiple Antenna Systems

Figure 5:
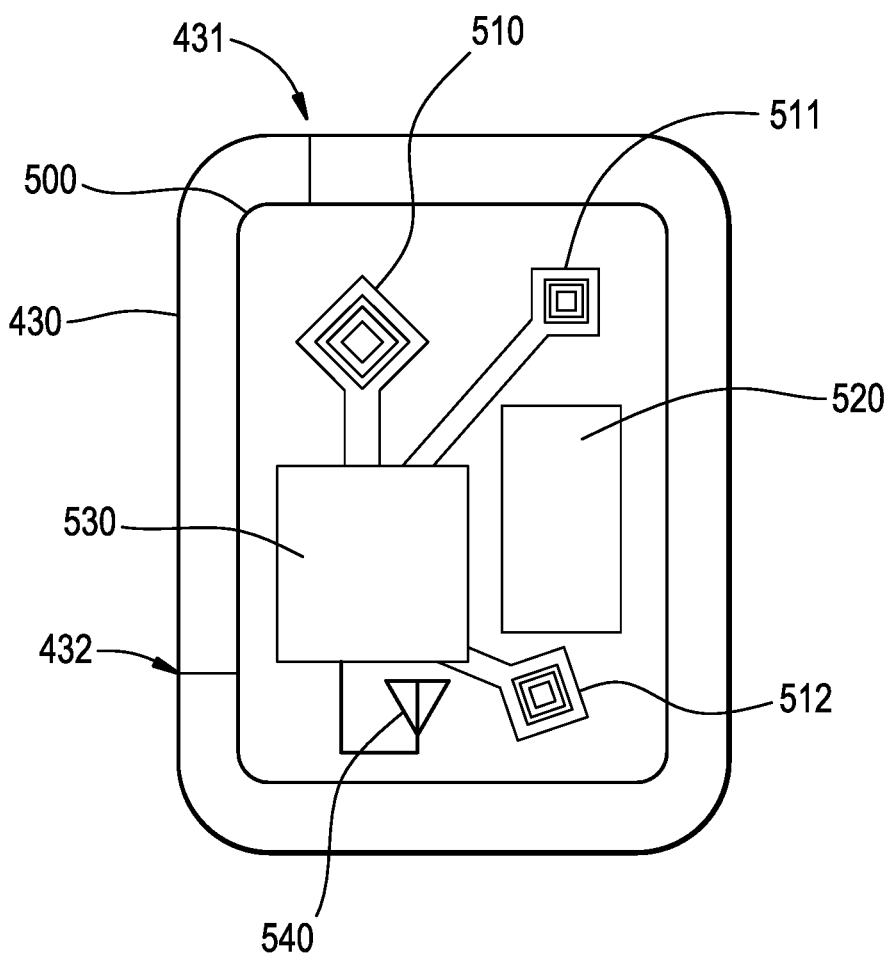
FIG. 5 illustrates an internal view of an exemplary embodiment of a sensor communication device in accordance with the present invention.

Referring to FIG. 5, an exemplary view of the internal structures of a sensor communication device 500 held in place by a bandage device 430 is illustrated. The bandage device 430 may have alignment marks as described with a first mark 431 and a second mark 432. The sensor communication device 500 may comprise an electrical circuit 530 which may comprise numerous functionality components such as a controller, a data storage device, a power management device, communications circuitry which may extract data from wireless signals received at transducers, and internal sensors of various kinds. The sensor communication device 500 may also comprise an energization element such as a single use or rechargeable battery 520. In some examples, the energy in the rechargeable battery 520 may be used to wirelessly charge devices in the orthopedic implant to energize or enable their ability to communicate data. The sensor communication device 500 may also comprise antennas optimized to communicate with the orthopedic implant. In some examples a single antenna may be used to communicate with the orthopedic implant. In FIG. 5 multiple antennas are configured to communicate with the orthopedic implant such as a first antenna 510, a second antenna 511, and a third antenna 512.

By incorporating a plurality of antennas numerous functions may be enabled. For example, the electrical circuit 530 may be able to receive the signals from the plurality of antennas and recognize the signal transmitted from the orthopedic implant which has crossed different paths to arrive at the different antennas. Signal to noise may be improved by sampling multiple signal paths and discriminating the common signal from the communication. In the process of transmitting data to the orthopedic implant, the electrical circuit 530 may be enabled to adjust power levels to the various antennas to enhance reception at the orthopedic implant. In still further use of a plurality of antennas, power may be transmitted from the sensor communication device 500 to the orthopedic implant. With directionally adjustable antennas for transmitters, the plurality of antennas may be used to triangulate a power signal directly to the receiving antenna of the orthopedic implant. Such a directional and localized beaming of power may enhance the efficiency of transfer as well as reducing the average power levels that traverse the various tissue layers between an orthopedic implant and a skin attached sensor communication device 500. In some examples, directional antennas may be directed towards a region by adjusting the physical structure of the antenna to point in different azimuthal orientations. The electrical circuit 530 may have feedback circuits that interact with the orthopedic implant. By communicating data related to the power level received at the orthopedic implant the orthopedic implant may together with the sensor communication device 500 hone in on optimal antenna connections for power transmission. In some examples, such a geometry and setup may also be optimal for data transmission as well.

The sensor communication device 500 may also include another antenna 540 that may be optimized for radiofrequency communication by the sensor communication device 500 to external devices capable of receiving the data stream. In some examples, the sensor communication device 500 may be a standalone device which may pair with a mobile phone in a Bluetooth standard pairing. In other examples, the sensor communication device 500 may be attached to a mobile phone where the transceiving capability of the mobile phone may take on the role of the antenna 540. In an alternative embodiment, a phased array antenna arrangement may be utilized.

In some examples, communication and/or energy transfer between the sensor communication device 500 may accomplished with other means than RF communication. In a non-limiting example, infrared light at frequencies which is relatively transparent to tissue layers may be used. In such examples, the roles of antennas may be replaced with combinations of infrared detectors and infrared light sources.

Other means of communicating signals and power may include ultrasound waves. In some examples using ultrasound waves for signal communication, conductive gels or other surface treatments may be used to enhance the effectiveness of communication from the external transducer to the implanted sensor devices.

Figure 6:
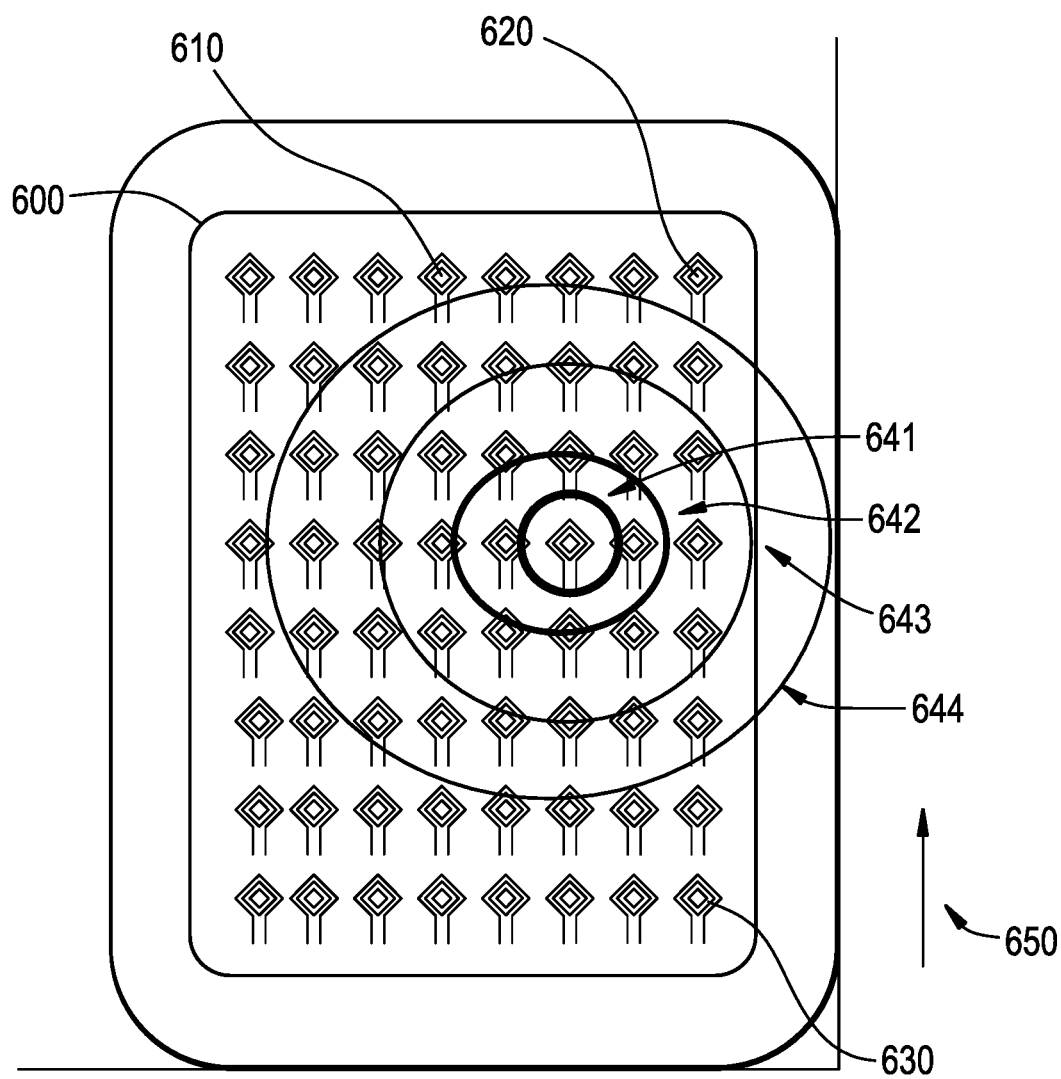
FIG. 6 illustrates an exemplary array of antenna devices in accordance with the present invention.

Referring to FIG. 6, an alternative depiction of a plurality of antenna being used in a communication system with an implanted device is illustrated. A layer 600 of the cuff device may include a plurality of minimally sized antennas across the surface of the device. Thus, one antenna 610 may be at the top of the cuff device while another antenna 620 may be at a corner and still another antenna 630 may be located at an opposite or bottom corner. As is shown, a plurality of the antennas may fill the entire surface of a layer of the cuff. The individual antennas may have individualized connections to switched circuits within the control electronics of the cuff. In some other examples, the antennas may operate in a grid where rastered reading of the values of the antenna may be obtained by connection of "row" and "column" connection lines that each connect to a multitude of antennas along their extent, but only connect to a single antenna in combination.

The matrix of antennas may be scanned for received signal strength (RS) and characterized as a matrix. The result of the scanning of the array may be an organization of arrays into levels of signal strength such as the strongest detected signal 641 at a particular antenna location, a band of nearby antennas with a reduced strength as region 642, a further band of antennas with further reduced strength as region 643 and a band of still further reduced strength region 644. It may be possible that some of the antennas shown outside of four regions 641-644 may have a negligible or zero RS. In some examples, it may be possible that for a given orientation such as that shown by vector 650 the signal level of the best RS region 641 and 642 may in fact be weaker than a best signal reception region when the cuff device is rotated around an axis. After such rotation, the region of strong signal strength may be expected to move within array of antenna elements. In some examples the shape of the regions may be altered as well. In some examples, signal processing systems may combine the signals of multiple antennas with time dependent signal processing or regional averaging to improve signal to noise aspects of data reception.

In some examples, an implanted sensor device may be removed from a patient after the healing process has proceeded to a sufficient or complete degree. The design of the sensor may be made for planned support of such a removal, and standard imaging techniques may support the removal. A matrix of antenna devices may be used to provide location information of the sensor, and a suitably equipped orthoscopic tool may include a transmitting device that may also be received by an antenna array device to guide movement of the orthoscopic tool during a removal process.

Figure 7:
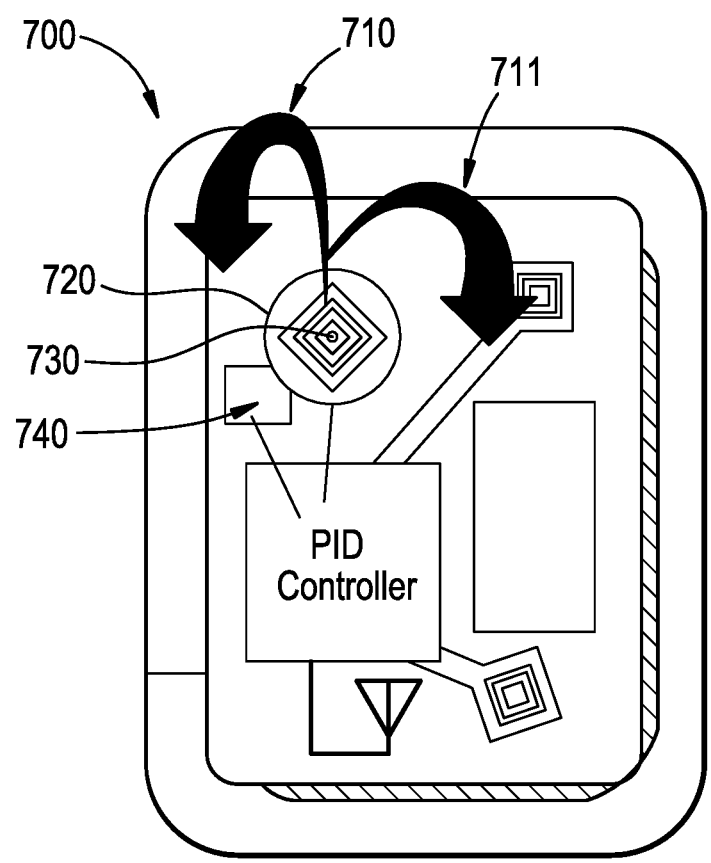
FIG. 7 illustrates an exemplary self-adjusting antenna structure in accordance with the present invention.

Proceeding to FIG. 7 a multiple antenna cuff type device 700 may include an antenna element that is mounted upon a stage 720 that has rotational and/or gimbling support that allows a level of automated rotation of the antenna device to occur. In some examples, electrical interconnections between the antenna and the outside world may occur through electrical contact points of a slip ring or other rotary electrical connection device. In other examples, a pair of wires capable of a limited amount of rotation may be fed through the axis of rotation 730. The movement of the stage 720 may occur in some examples for a rotation in a counter clockwise 710 or clockwise 711 direction and may be driven by a rotary driver 740. In some examples the rotary driver 740 may include PID circuitry to respond with feedback to a detected received signal level RS. The operation of this automated rotation may occur as has been described in relationship to FIG. 4D. The result may be a continuous and automated optimization of the received signal level. If the device is configured to gimble, it may be apparent that the rotary drive may also include the ability to move in an azimuthal direction as well. The PID controller would in such circumstances also integrate two output signals into the algorithmic response. It may be possible that a cuff device with automatic signal enhancement may still benefit from a user-controlled rotation of the overall device as has been described, where the proximity of the stage 720 may be moved closer to a transmitter by a gross movement of the cuff device.

Detection of Infectious States

A bone infection or osteomyelitis not only impedes proper healing but may also pose serious health risks in general. Osteomyelitis is an infection in the bone and can occur in individuals of any age and be caused by various means such as bacteria in the bloodstream, from an open wound, for example, a compound fracture, and recent surgery or injection in or around the bone. There are a number of tests that may be utilized to detect osteomyelitis, including scans and blood tests. However, sensors located near the fracture site may provide an indication of infection before typical symptoms occur. Localized sampling of the tissue and fluids may be rapidly analyzed.

The prognosis for osteomyelitis is good when detection and treatment is early. If there is a long delay in the diagnosis and thus the treatment of osteomyelitis, there is a chance for significant bone and soft tissue injury. This may lead to long-term and/or permanent functional deficits and/or increase the risk of fracture reoccurrence. Accordingly, the sensors of the present invention allow for the earliest possible detection through detection of agents within the blood or surrounding tissue.

In some examples the bone implant may incorporate multiple sensors. As mentioned previously these multiple sensors may include one or more of a pressure sensor, a load sensor, a temperature sensor, a pH sensor, and an oximetry sensor. These sensors may be powered by an energization element on the orthopedic implant that receives charging as mentioned herein. The results of these sensors may be communicated to the sensor communication device 500 in the means as discussed. The resulting data stream may be analyzed by upstream processors and/or may be communicated to medical professionals who may be able to utilize the combination of sensor data to diagnose good or poor healing progression based on the various sensing results. The sensing results may be time stamped and married to other sensing devices such as accelerometers and GPS transceivers that may be located in the sensor communication device 500 or in other wearable devices of the user. By combining information such as accelerometer data with the sensors correlated to healing, medical professionals may be able to deduce that particular types of activity or lack thereof are positive or negative to the healing of the damage in the region of the orthopedic implant and suggest modifications as appropriate.

In some examples, sensors may be incorporated which are created and/or trained to detect biomarkers that are associated with specific biological organisms. As a non-limiting example, a sensor incorporating an array of photosensitive devices each trained for different spectral regions and responses may include a processor utilizing artificial intelligence algorithms which is programmed or learns to detect a distinct chemical signature of an invasive organism's presence or growth.

Figure 8A:
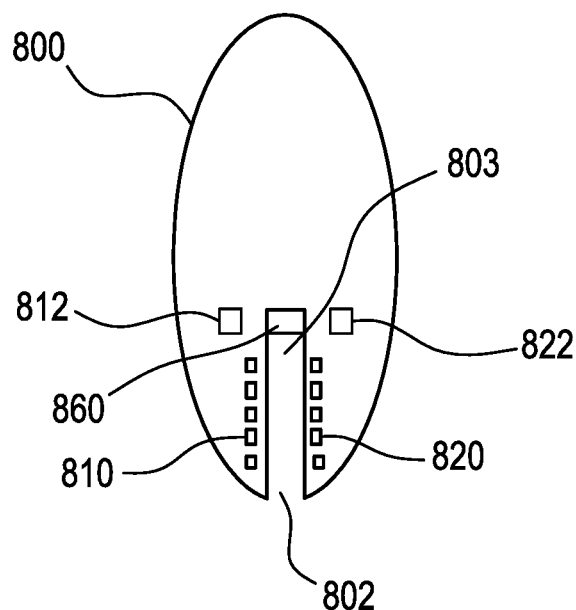
FIGS. 8A-8C illustrate a quantum dot spectroscopic analysis device in accordance with the present invention.
Figure 8B:
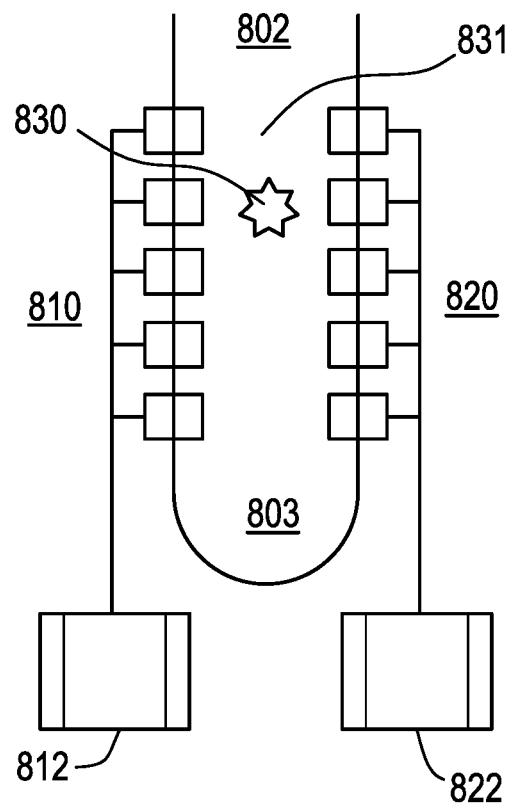
Figure 8C:
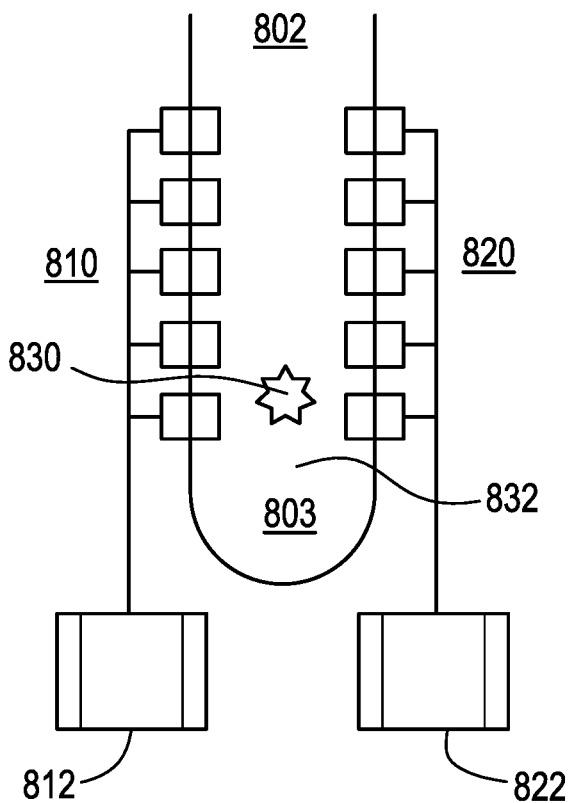

Referring to FIGS. 8A-8C, an exemplary photo-absorption based sensor is illustrated. FIG. 8A illustrates an exemplary quantum dot (QD) spectrometer system incorporated into an implanted sensor upon a bone as a biomedical device 800. The illustration in FIG. 8A may utilize a passive approach to collecting samples wherein a sample fluid passively enters a channel 802. The channel 802 may be internal to the biomedical device 800 in some examples and in other examples, as illustrated, the biomedical device 800 may surround an external region with a reentrant cavity. In some examples where the biomedical device 800 creates a channel of fluid external to itself, the device 800 may also contain a pore 860 to emit reagents or dyes to interact with the external fluid in the channel region. An analysis region 803 may comprise a reentrant channel 802 within the sensor device that allows external fluid to passively flow in and out of the channel. When an analyte, for example, in fluid surrounding the orthopedic implant, diffuses or flows into the channel 802 it becomes located between the analysis region 803 as depicted in FIG. 8A.

Referring now to FIG. 8B, once an analyte diffuses or otherwise enters the quantum-dot spectrometer channel which shall be referred to as the channel 802, a sample 830 may pass in the emission portion of a quantum-dot (QD) emitter 810. The QD emitters 810 may receive information from a QD emitter controller 812 instructing the QD emitters 810 to emit an output spectrum of light across the channel 802.

In some examples, the QD emitter 810 may act based on emission properties of the quantum-dots. In other examples, the QD emitter may act based on the absorption properties of the quantum-dots. In the examples utilizing the emission properties of the quantum-dots, these emissions may be photostimulated or electrically stimulated. In some examples of photostimulation; energetic light in the violet to ultraviolet may be emitted by a light source and absorbed in the quantum-dots. The excitation in the QD may relax by emitting photons of characteristic energies in a narrow band. As mentioned previously, the QDs may be engineered for the emission to occur at selected frequencies of interest.

In a similar set of examples, QDs may be formed into a set of layers. The layers may place the QDs between electrically active layers that may donate electrons and holes into the QDs. These excitations, due to the donations of electrons and holes may similarly stimulate the QDS to emit characteristic photons of selected frequency. The QD emitter 810 may be formed by inclusion of nanoscopic crystals, that function as the quantum-dots, where the crystals may be controlled in their growth and material that are used to form them before they are included upon the emitter element.

In an alternative set of examples, where the QDs act in an absorption mode a combination of a set of filters may be used to determine a spectral response in a region. Combinations of QD absorption elements may be used in analysis to select regions of the spectrum for analysis.

In either of these types of emission examples, a spectrum of light frequencies may be emitted by QD emitter 810 and may pass thru the sample 830. The sample 830 may absorb light from some of the emitted frequencies if a chemical constituent within the sample is capable of absorbing these frequencies. The remaining frequencies that are not absorbed may continue on to the detector element, where QD receivers 820 may absorb the photons and convert them to electrical signals. These electrical signals may be converted to digital information by a QD detector sensor controller 822. In some examples the sensor controller 822 may be connected to each of the QD receivers 820, or in other examples the electrical signals may be routed to centralized electrical circuits for the sensing. The digital data may be used in analyzing the sample 830 based on predetermined values for QD wavelength absorbance values.

In FIG. 8C, the QD system is depicted in a manner where the sample is passed in front of spectral analysis elements that are spatially located. In some examples, the sample 830 may contain analytes that diffuse inside a region of a biomedical device that encloses external fluid with material of the biomedical device to form a pore or cavity into which the sample may passively flow or diffuse to an analytical region that passes light from emitters within the sensor device, through interstitial fluid surrounding the orthopedic implant, and again to detectors within the sensor device. FIGS. 8B and 8C depict such movement as the difference between the locations of the sample 830 which has moved from a first location 831 along the analysis region to the new location 832. In other examples the QDs may be consolidated to act in a single multidot location where the excitation means and the sensing means are consolidated into single elements for each function. A sensor device on an orthopedic implant may have sufficient space for hundreds of quantum-dot devices which allow for a full spectrographic characterization of analyte containing mixtures.

Although shown and described in what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated but should be constructed to cohere with all modifications that may fall within the scope of the appended claims.

What is claimed is:

1. An apparatus for positioning a sensor communication device, the apparatus comprising:
    a first band of flexible material comprising a first portion of a fastening device;

a second band of flexible material comprising a second portion of the fastening device, wherein engagement of the first portion of the fastening device with the second portion of the fastening device holds the apparatus for positioning the sensor communication device in place in close proximity to an orthopedic implant of a patient;

a support structure, wherein a first side of the support structure is affixed to an edge of the first band of flexible material and a second side of the support structure is affixed to an edge of the second band of flexible material, the first side of the support structure is in a distal configuration to the second side of the support structure and the sensor communication device is held by the support structure, and the sensor communication device is configured to communicate one or more of data or power to the orthopedic implant of the patient; and the sensor communication device further comprises:

an antenna system having a plurality of antennas that are configured to communicate the one or more of power or data to the orthopedic implant and an electrical circuit configured to control communication and adjust a directional position and a power level of each of the plurality of antennas, wherein the support structure is further configured to allow the sensor communication device to be rotated around an axis based upon analysis of sensed communication signals to determine an orientation of the sensor communication device relative to the orthopedic implant that corresponds to maximal signal to noise and an algorithmic analysis of a combined signal strength of the signals of the plurality of antennas generates the maximal signal to noise of a received signal level of the combined plurality of antennas.

2. The apparatus for positioning the sensor communication device according to claim 1, wherein the sensor communication device comprises a display screen configured to provide feedback to a user to adjust a rotational position of the sensor communication device, and the adjustment optimizes signal communication between the sensor communication device and the orthopedic implant.

3. The apparatus for positioning the sensor communication device according to claim 1, further comprising:
a sensor configured to detect osteomyelitis.

4. An apparatus for positioning a sensor communication device, wherein the sensor communication device comprises an antenna system having a plurality of antennas that are configured to communicate one or more of power or data to an orthopedic implant of a patient, the apparatus comprising:

a first band of flexible material comprising a first portion of a fastening device;

a second band of flexible material comprising a second portion of the fastening device, wherein engagement of the first portion of the fastening device with the second portion of the fastening device holds the apparatus for positioning the sensor communication device in place in close proximity to the orthopedic implant of the patient;

a support structure, wherein a first side of the support structure is affixed to an edge of the first band of flexible material and a second side of the support structure is affixed to an edge of the second band of flexible material, the first side of the support structure is in a distal configuration to the second side of the support structure and the sensor communication device is held by the support structure, and the sensor communication device further comprises:

a display screen configured to provide feedback to a user to adjust a rotational position of the sensor communication device based upon analysis of sensed communication signals to determine an orientation of the sensor communication device relative to the orthopedic implant that corresponds to maximal signal to noise, an algorithmic analysis of a combined signal strength of the signals of the plurality of antennas generates the maximal signal to noise of a received signal level of the combined plurality of antennas, and the adjustment optimizes signal communication between the sensor communication device and the orthopedic implant.

5. The apparatus for positioning the sensor communication device according to claim 4, wherein the sensor communication device comprises an electrical circuit that is configured to control communication and adjust a power level of each of the plurality of antennas.

6. The apparatus for positioning the sensor communication device according to claim 5, wherein the sensor communication device comprises an antenna configured to communicate in a wireless protocol with a data processing device, server, smart device, or mobile communication device.

7. The apparatus for positioning the sensor communication device according to claim 6, wherein the sensor communication device further comprises:
an antenna supported upon a movable substrate that is configured to rotate around an axis;
an electroactive element configured to cause rotation of the movable substrate; and
a Proportional Integral Derivative (PID) controller configured to follow an inputted received signal of the antenna and generate a first movement signal.

8. The apparatus for positioning the sensor communication device according to claim 7, wherein the feedback to the user to adjust a rotational position of the sensor communication device causes a global movement of the plurality of antennas; and a subsequent received signal level of the antenna on the rotatable substrate is processed by the PID controller to generate a second movement signal.

9. The apparatus for positioning the sensor communication device according to claim 6, wherein the sensor communication device further comprises:
an antenna supported upon a moveable substrate that is configured to gimble with rotations around at least a first and a second axis;
a first electroactive element configured to cause rotation of the movable substrate around the first axis;
a second electroactive element configured to cause rotation of the movable substrate around the second axis; and
a Proportional Integral Derivative (PID) controller configured to follow an inputted received signal, a feedback of the control signal to the first electroactive element, and a feedback of the control signal to the second electroactive element to generate a vector array of movement signals to the first electroactive element and the second electroactive element.

10. The apparatus for positioning the sensor communication device according to claim 5, wherein the feedback to the user to adjust a rotational position of the sensor communication device causes a global movement of the plurality of antennas and the maximal signal to noise is used to adjust the feedback to the user to adjust a rotational position of the sensor communication device.

11. The apparatus for positioning the sensor communication device according to claim 5, wherein the feedback to the user to adjust a rotational position of the sensor communication device causes a global movement of the plurality of antennas; and an algorithmic analysis of signal strength of the signals of the plurality of antennas generates a determination of a highest signal strength antenna of the plurality of antennas and the result of the algorithmic analysis causes the system to isolate connections to the highest signal strength antenna causing the highest signal strength antenna to be the antenna used for transmission to the orthopedic implant.

12. An apparatus for positioning a sensor communication device, wherein the sensor communication device comprises an antenna system having a plurality of antennas that are configured to communicate one or more of power or data to an orthopedic implant of a patient, the apparatus comprising:
an adhesive layer, wherein the adhesive attaches to a user's skin and may be released with an amount of force safe for the user's skin, wherein the adhesive holds the apparatus for positioning the sensor communication device in place on the user's skin in close proximity to the orthopedic implant of the patient;
a support structure, wherein a first side of the support structure is in contact with the adhesive layer and a second side of the support structure provides a support layer for the sensor communication device and the sensor communication device is held by the support structure, the sensor communication device is configured to communicate one or more of data or power to the orthopedic implant of the patient, the support structure is configured to be rotated around an axis held in place by the adhesive layer, and the sensor communication device is configured to display feedback information to align the apparatus for positioning the sensor device for optimal signal strength based upon analysis of sensed communication signals to determine an orientation of the sensor communication device relative to the orthopedic implant that corresponds to maximal signal to noise and an algorithmic analysis of a combined signal strength of the signals of the plurality of antennas generates the maximal signal to noise of a received signal level of the combined plurality of antennas.

13. The apparatus for positioning the sensor communication device according to claim 12, wherein the sensor communication device comprises an electrical circuit configured to control communication and adjust a directional position and a power level of each of the plurality of antennas.

14. The apparatus for positioning the sensor communication device according to claim 12, wherein the sensor communication device further comprises:
an antenna supported upon a movable substrate that is configured to rotate around an axis;
an electroactive element configured to cause rotation of the movable substrate; and
a Proportional Integral Derivative (PID) controller configured to follow an inputted received signal of the antenna and generate a first movement signal.

15. The apparatus for positioning the sensor communication device according to claim 14, wherein the feedback to the user to adjust a rotational position of the sensor communication device causes a global movement of the plurality of antennas, and a subsequent received signal level of the antenna on the rotatable substrate is processed by the PID controller to generate a second movement signal.

16. The apparatus for positioning the sensor communication device according to claim 12, wherein the feedback to the user to adjust a rotational position of the sensor communication device causes a global movement of the plurality of antennas and the maximal signal to noise is used to adjust the feedback to the user to adjust a rotational position of the sensor communication device.

17. The apparatus for positioning the sensor communication device according to claim 16, wherein the sensor communication device comprises a display screen configured to provide feedback to a user to adjust a rotational position of the sensor communication device, and the adjustment optimizes signal communication between the sensor communication device and the orthopedic implant.

18. A method of receiving data from an orthopedic implant, the method comprising:
placing an apparatus for positioning a sensor communication device in proximity to the orthopedic implant, which has been implanted into a patient;
holding a sensor communication device with the apparatus for positioning the sensor communication device, wherein the sensor communication device comprises an antenna system having a plurality of antennas that are configured to communicate one or more of power or data to the orthopedic implant of the patient;
providing a signal from the sensor communication device to the orthopedic implant, wherein the signal initiates the orthopedic implant to send out a communication:
receiving a signal from the orthopedic implant to the sensor communication device;
rotating the sensor communication device around an axis, wherein the signal from the orthopedic implant is continuously sensed by the sensor communication device;
analyzing the sensed communication signals to determine an orientation of the sensor communication device relative to the orthopedic implant that corresponds to maximal signal to noise, wherein analysis of a combined signal strength of the signals of the plurality of antennas generates the maximal signal to noise of a received signal level of the combined plurality of antennas;
displaying a message to a user to rotate the sensor communication device; rotating the sensor communication device;
displaying a message to the user when the rotation is at the maximal position to suspend moving the device; and
receiving a communication from the orthopedic implant of a result from a sensor on the orthopedic implant.

19. The method of claim 18, wherein the sensor communication device is configured to control both direction and power applied to the plurality of antennas.

20. The method of claim 19, further comprising:
marking the skin of a patient with an alignment marking; and
aligning the alignment marking with a marking on the apparatus for positioning the sensor communication device.

* * * * *